(12) United States Patent
Bierl et al.

(10) Patent No.: US 9,194,835 B2
(45) Date of Patent: Nov. 24, 2015

(54) METHOD AND DEVICE FOR DETERMINING A FUEL PORTION IN A MOTOR OIL OF A MOTOR VEHICLE

(75) Inventors: Rudolf Bierl, Regensburg (DE); Philippe Grass, Regensburg (DE); Jan Haag, Nittenau (DE); Armin Hollstein, Regensburg (DE); Denny Schädlich, Neustadt (DE)

(73) Assignees: Continental Automotive GmbH, Hannover (DE); Continental Automotive France, Toulouse (FR)

( * ) Notice: Subject to any disclaimer, the term of this patent is extended or adjusted under 35 U.S.C. 154(b) by 436 days.

(21) Appl. No.: 12/742,353

(22) PCT Filed: Nov. 10, 2008

(86) PCT No.: PCT/EP2008/065234
§ 371 (c)(1),
(2), (4) Date: May 11, 2010

(87) PCT Pub. No.: WO2009/062913
PCT Pub. Date: May 22, 2009

(65) Prior Publication Data
US 2010/0253371 A1 Oct. 7, 2010

(30) Foreign Application Priority Data

Nov. 16, 2007 (DE) .................. 10 2007 054 858

(51) Int. Cl.
*G01N 27/22* (2006.01)
*G01N 33/28* (2006.01)
(52) U.S. Cl.
CPC ............ *G01N 27/22* (2013.01); *G01N 33/2888* (2013.01)

(58) Field of Classification Search
CPC .................................................. G01R 27/2605
USPC ........................... 324/663, 667, 698; 73/304, 73/53.01–53.09
See application file for complete search history.

(56) References Cited

U.S. PATENT DOCUMENTS

| | | | |
|---|---|---|---|
| 4,646,070 A * | 2/1987 | Yasuhara et al. | 340/603 |
| 6,853,203 B2 | 2/2005 | Beylich et al. | |
| 7,106,075 B2 | 9/2006 | Hu | |
| 7,479,091 B2 * | 1/2009 | Yang | 477/108 |
| 7,581,434 B1 * | 9/2009 | Discenzo et al. | 73/53.01 |
| 2002/0011095 A1 | 1/2002 | Park et al. | |
| 2003/0222656 A1 | 12/2003 | Phillips et al. | |
| 2004/0239344 A1 | 12/2004 | Hu | |
| 2006/0229776 A1 * | 10/2006 | Lvovich et al. | 701/29 |

FOREIGN PATENT DOCUMENTS

| | | | |
|---|---|---|---|
| DE | 100 00 148 A1 | | 7/2001 |
| DE | 100 25 690 A1 | | 11/2001 |
| DE | 102 08 600 A1 | | 9/2003 |
| FR | WO2007051941 | * | 10/2007 |
| WO | WO 03/014729 | | 2/2003 |

* cited by examiner

Primary Examiner — Arleen M Vazquez
Assistant Examiner — Feba Pothen
(74) Attorney, Agent, or Firm — Cozen O'Connor

(57) ABSTRACT

A method and device for determining a fuel portion in a motor oil of a motor vehicle. The motor oil is brought between at least two electrodes forming a capacitor. The capacitance of the capacitor is determined while the motor oil is located between the electrodes, and the fuel portion in the motor oil is determined from the capacitance of the capacitor.

14 Claims, 2 Drawing Sheets

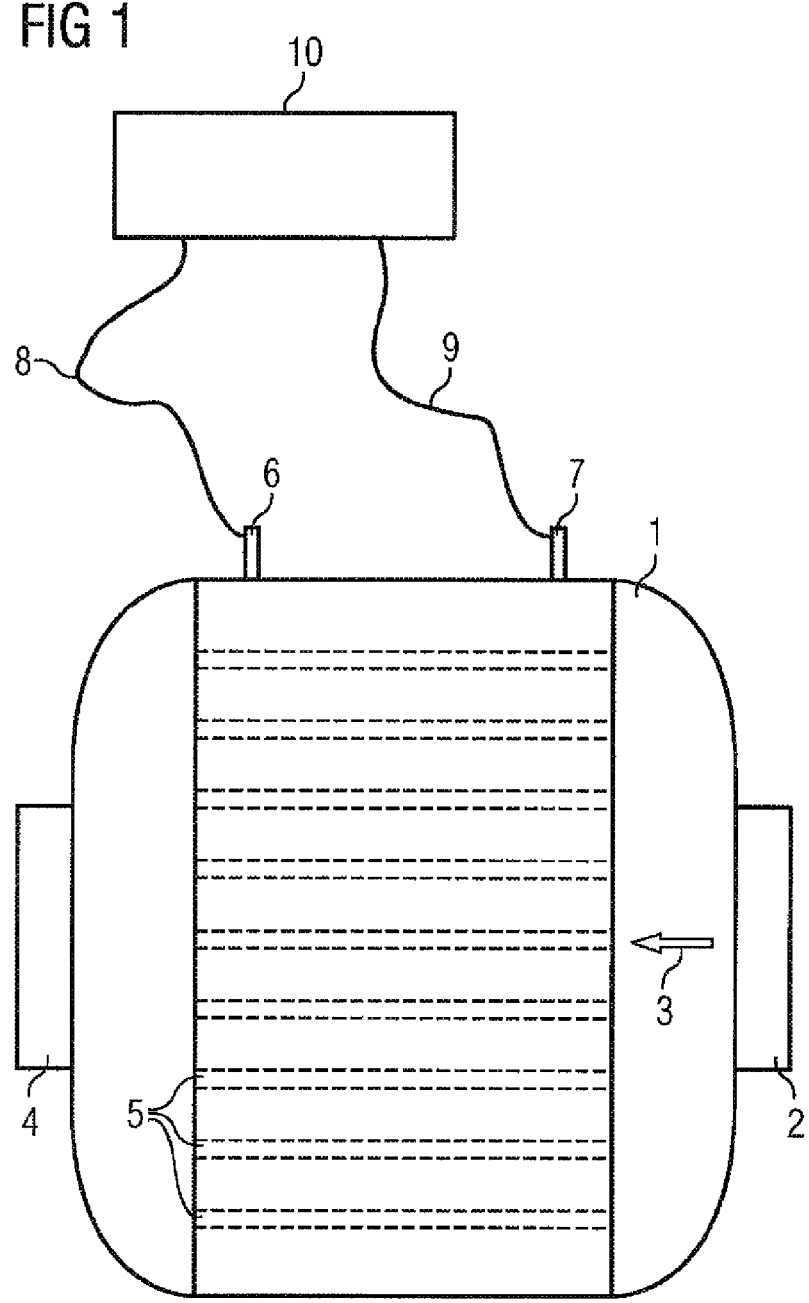

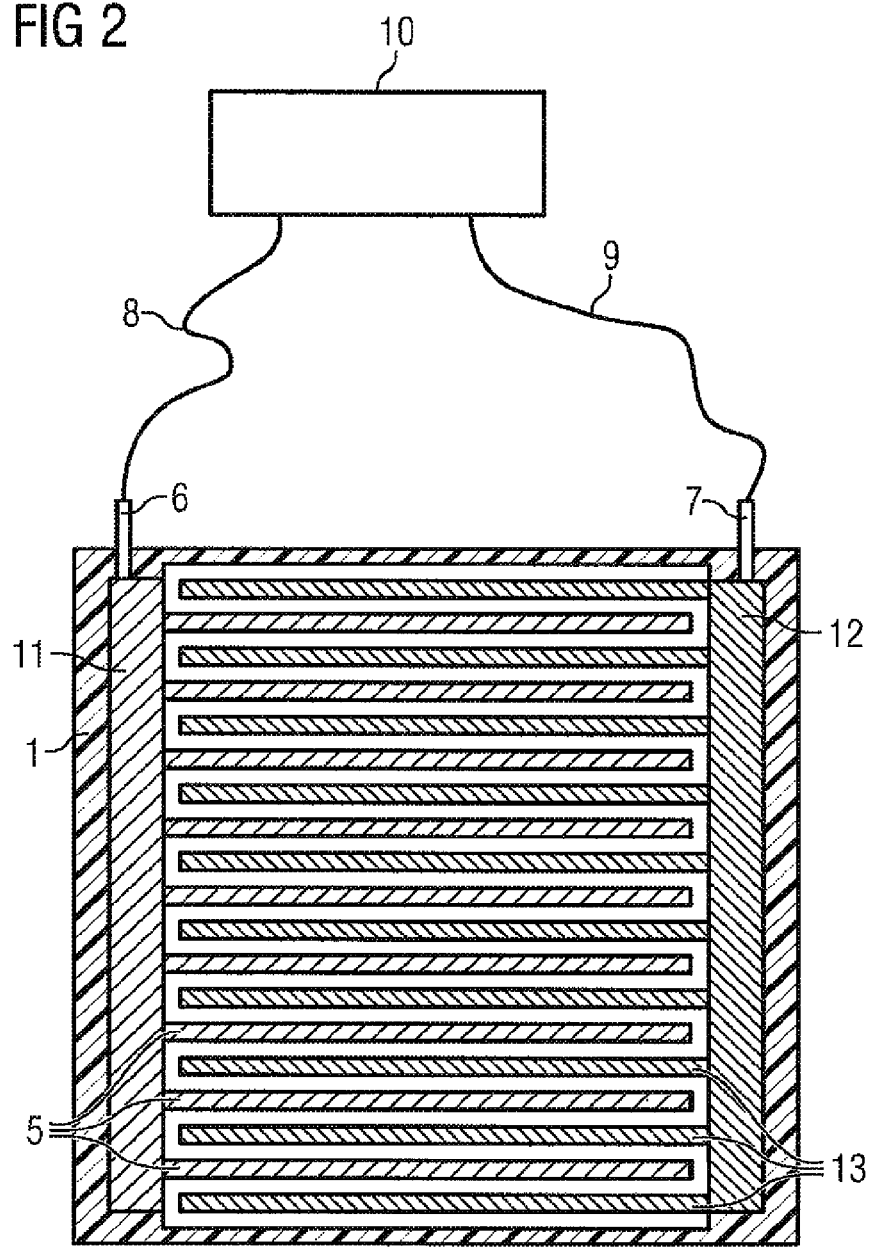

METHOD AND DEVICE FOR DETERMINING A FUEL PORTION IN A MOTOR OIL OF A MOTOR VEHICLE

PRIORITY CLAIM

This is a U.S. national stage of application No. PCT/EP2008/065234, filed on Nov. 10, 2008 which claims priority to the German Application No.: 10 2007 054 858.5, filed: Nov. 16, 2007; the contents of which are incorporated here by reference.

BACKGROUND OF THE INVENTION

1. Field of the Invention

The present invention relates to a method and a device for determining a fuel portion (i.e., percentage or ratio) in an engine oil of a motor vehicle.

2. Prior Art

During operation of internal combustion engines of motor vehicles, fuel can enter the engine oil. This risk occurs in particular before the engine has reached its operating temperature, that is to say in the cold state. Before the operating temperature of the internal combustion engine is reached there is often incomplete combustion of the supplied fuel. The fuel can then precipitation the cylinder walls and enter the engine oil. Furthermore, in the cold state of the engine there are air gaps between engine components as a result of which the unburned fuel can enter the engine oil. Owing to their non-volatile components this problem occurs in particular with diesel fuels. In this context fuel can particularly frequently enter the engine oil in the case of what are referred to as bio-diesel fuels, that is to say diesel fuels on a plant basis, which are acquired from plant oils or animal fats since these fuels likewise do not always burn completely when the operating temperature of the internal combustion engine is reached.

The engine oil performs a multiplicity of important tasks in an internal combustion engine. The engine oil serves predominantly to lubricate the parts which move in relation to one another in internal combustion engines. Furthermore, friction heat is carried away by the engine oil, impurities are washed out, and metal parts are protected against corrosion. The fuel that enters the engine oil greatly increases the engine wear, often accompanied by an increase in the fuel consumption and the emission of pollutants by the internal combustion engine.

In order to solve this problem, in the past the engine oil changing intervals have been correspondingly shortened when bio-fuels are used. However, before the oil change it is not possible to obtain information as to whether the oil change is actually necessary at this time owing to an increased fuel portion in the engine oil. Unnecessary oil changes are therefore carried out under certain circumstances.

SUMMARY OF THE INVENTION

Taking the prior art explained above as the starting point, an embodiment of the invention is based at least in part on specifying a method and a device with which the fuel portion in the engine oil can easily be determined so that an excessively high fuel portion in the engine oil can be detected.

According to one embodiment of the invention, a method for determining a fuel portion in an engine oil of a motor vehicle, in which the engine oil is placed between at least two electrodes which form a capacitor. The capacitance of the capacitor is determined while the engine oil is located between the electrodes, and the fuel portion in the engine oil is determined from the capacitance of the capacitor.

The object is achieved by a device for determining a fuel portion in an engine oil of a motor vehicle, having at least two electrodes form a capacitor and between which the engine oil can be placed. An evaluation device with which the capacitance of the capacitor can be determined while the engine oil is located between the electrodes, and with which the fuel portion in the engine oil can be determined from the capacitance of the capacitor.

The invention is based at least in part on of measuring the fuel portion in the engine oil capacitively. The invention is based on different types of fuel and different types of oil having different dielectric constants. The dielectric constant of the engine oil therefore changes as the fuel portion in the oil increases. To determine the dielectric constant, the engine oil to be measured is placed in a measuring cell in the sensor, which measuring cell forms a capacitor. A change in the dielectric constant of the engine oil which is located between the capacitor electrodes leads correspondingly to a change in the dielectric of the capacitor and therefore to a change in the capacitance of the capacitor. Conclusions can therefore be drawn about the fuel portion located in the engine oil by measuring the capacitance of the capacitor while the engine oil is located between the capacitor electrodes. In particular, contamination of the engine oil with fuel can be reliably and precisely detected with the method according to one embodiment of the invention and the device according to one embodiment of the invention. It is therefore possible to take suitable measures when a maximum contamination of the fuel, a limiting value, is exceeded. These measures include, for example, sending corresponding information to the motor vehicle driver or to a workshop, for example within the scope of an inspection of the vehicle.

The design of the sensor according to one embodiment of the invention for measuring a fuel portion in an engine oil is particularly simple and therefore cost-effective. Accordingly, with the method it is possible to determine the fuel portion in the engine oil in a particularly simple and cost-effective way.

According to one embodiment of the invention, the engine oil is placed between the electrodes. In this context it can be removed from the space between the electrodes at a later time. The engine oil can be directed through between the electrodes. Directing the oil through between the electrodes in this context that the oil is placed between the electrodes for measurement and removed again from the sensor at a later time.

The engine oil can be placed between the capacitor electrodes in the scope of the normal oil circulation. For this purpose, the sensor can be suitably placed in the oil circuit, in particular arranged therein. In this case, the oil therefore flows through between the electrodes in the scope of its normal circulation. Of course, it is basically also conceivable to provide a separate device for placing the engine oil between the electrodes, for example, a suitable pump.

It is also conceivable to dip the sensor into the engine oil for the measurement and to place the oil between the electrodes in this way. The sensor according to one embodiment of the invention can also be arranged in an oil sump of the internal combustion engine, and the engine oil can in this way be placed between the electrodes. In this case, the sensor is not integrated into a circulation system. The entry and discharging of the engine oil into the sensor and out of the sensor and in particular between the electrodes then take place by convection in the oil sump.

It is possible to compare the capacitance of the capacitor measured during operation with a capacitance measured in the scope of a preceding calibration with a pure engine oil, that is to say one which is not contaminated with a fuel. On this basis, the degree of contamination of the fuel can be detected particularly easily.

To determine the capacitance of the capacitor, it is possible to apply an electrical voltage, in particular an alternating voltage, to the capacitor electrodes. For this purpose, the device can have a suitable voltage supply. The determination of the capacitance of capacitors is known per se to a person skilled in the art and will therefore not be explained in more detail here.

In the present context, the term determination of the capacitance also includes, of course, the determination of a variable which correlates to the capacitance of the capacitor. Of course, it is also possible to determine the fuel portion in the oil from such a variable of the capacitor which correlates to the capacitance.

According to one embodiment of the invention, the fuel portion can be a diesel fuel portion. The internal combustion engine can therefore be a diesel internal combustion engine. Owing to their non-volatile components there is a risk, in particular, with diesel fuels of the problem of the fuel entering the engine oil so there is an urgent requirement to detect the fuel portion in the engine oil.

It is, of course, also conceivable that the fuel portion in the engine oil is a gasoline fuel portion, that is to say a fuel for a spark-ignition internal combustion engine. In this case, the internal combustion engine can be a spark-ignition internal combustion engine.

According to one embodiment, the fuel portion can be a bio-fuel portion, in particular a bio-diesel fuel portion. Such fuels on a plant basis also do not burn completely in some cases at the operating temperature of the internal combustion engine. As a result, the fuel can enter the engine oil. Accordingly, it is particularly important to monitor the fuel portion in the oil. Furthermore, a bio-fuel, in particular a bio-diesel fuel in the engine oil can be determined particularly well by a capacitance measurement since the dielectric constants of bio-fuel differ particularly significantly from the dielectric constants of engine oils. In particular, this difference is greater than, between mineral diesel fuel and mineral engine oil.

According to one embodiment of the method, alternating voltages of different frequencies can be applied to the capacitor electrodes and the impedance of the capacitor can be determined in each case. According to this embodiment of the device, a voltage supply can be provided with which alternating voltages of different frequencies can be applied to the capacitor electrodes, wherein in each case the impedance of the capacitor can be determined with the evaluation device. The electrical alternating voltages are applied here while the engine oil is located between the electrodes. The impedance is frequency-dependent. The determination of the impedance is known per se to a person skilled in the art and is therefore not explained in more detail. According to this embodiment, an alternating voltage frequency range is therefore moved through and a corresponding impedance spectrum is recorded. Particularly precise information about the fuel portion in the engine oil can be acquired from this. In particular it is then possible to identify the type of fuel present in the engine oil from the impedance values at different alternating voltage frequencies. This identification of the fuel can be carried out with the evaluation device. This refinement is based on the realization that different fuels act on the impedance in different ways at different alternating voltage frequencies. Different fuels can be identified from an evaluation of the recorded impedance spectrum, for example the position and/or the level of maxima (peaks) and minima etc. It is possible in this way to detect, for example, whether the fuel present in the engine oil is a mineral diesel fuel or a bio-diesel fuel. For the purpose of evaluation, the recorded impedance spectrum can be compared with reference spectrums previously obtained for known levels of contamination with fuel.

According to one embodiment which is particularly close to practical conditions, the engine oil can be placed between a plurality of electrodes which form a capacitor. In this refinement of the device, a multiplicity of electrodes which form a capacitor may be provided. A multiplicity of capacitor electrodes can be used to form a capacitor with a particularly large capacitance per volume. As a result, correspondingly high capacitance measurement values are available in terms of absolute values. For example, induced extraneous fields can only exert a small influence on the measurements. As a result, particularly and correspondingly expensive screening measures can be dispensed with. If a plurality of electrodes are provided they can, in particular, have a double-sided action. For this purpose, an electrical voltage is respectively provided between adjacent electrodes. Adjacent electrodes are therefore connected to a different electrical potential. In this context, every second electrode can be respectively connected to the same potential. In this way, only one voltage supply with two electrical terminals is necessary for all the capacitor electrodes.

The capacitor electrodes can be capacitor plates. The embodiment of the electrodes in plate form leads to a particularly simple design of the capacitor. The plates are then arranged parallel to one another and are at a distance from one another at which the dielectric of the capacitor is located, with adjacent plates being connected to a different electrical potential.

In particular, if a multiplicity of capacitor plates, between which the engine oil is placed for measurement, are provided, these capacitor plates can be arranged in parallel and spaced apart from one another. The plates can therefore be arranged stacked at a distance from one another. In this context, adjacent electrodes are connected to a different electrical potential. These electrodes which are connected to a different potential may engage in one another in a comb shape here. Every second plate is then respectively connected to the same potential. This in turn results in a particularly simple design in which only one voltage supply with two electrical terminals for all the plates is necessary. Of course, the electrodes can also be of a different shape, and may be, for example, embodied in a cylindrical fashion. These cylindrical electrodes can then have a different diameter and be arranged pushed one into the other. An electrical voltage can then be respectively applied between adjacent cylinders.

BRIEF DESCRIPTION OF DRAWINGS

An exemplary embodiment of the invention is explained in more detail below with reference to a drawing, in which, in each case in schematic form:

FIG. 1 is a device according to one embodiment of the invention in a side view; and FIG. 2 is a sectional view of the device illustrated in FIG. 1.

DETAILED DESCRIPTION OF THE DRAWINGS

In the figures, identical reference symbols denote identical subject matters. FIG. 1 is a device according to one embodiment of the invention for measuring a fuel portion in an engine oil of a motor vehicle in a side view. The device has a housing 1, preferably made of plastic. An inlet opening 2 for the engine oil to be examined is provided on the housing 1. For the purpose of measurement, the engine oil can be directed through the inlet opening 2 into the device. In the illustrated example, the device is integrated into the oil circulation of the engine. The engine oil then flows through the device as indicated by the arrow 3 in FIG. 1.

After passing through the device, the engine oil exits from the device again at an outlet opening 4 lying opposite the inlet opening 2. The engine oil, which is directed through the device is, in the illustrated example, an engine oil of a diesel internal combustion engine. In the illustrated example, said engine oil is contaminated by a bio-diesel fuel portion.

In the illustrated example, the device has a multiplicity of plate-shaped electrodes which form a capacitor. In FIG. 1 only a number of these electrodes 5 which are located behind the wall of the housing 1, are illustrated schematically. The engine oil flows correspondingly through in the direction of the arrow 3 between these electrodes 5 which form a capacitor. A common voltage supply is provided for supplying the capacitor plates with an electrical voltage. Said voltage supply has two electrical terminals 6, 7. The electrical terminals are respectively connected via electrical lines 8, 9 to an evaluation device 10 into which the voltage supply is also preferably integrated.

The design of the capacitor plates of the device according to the invention can be seen in FIG. 2. FIG. 2 illustrates the device according to one embodiment of the invention in a view with a section perpendicular to the direction of flow 3 of the engine oil. In FIG. 2, the engine oil flows through the device in a perpendicular direction with respect to the plane of the drawing. The electrical terminals 6, 7 are respectively connected to a first terminal plate 11 and a second terminal plate 12 of the capacitor. A multiplicity of first capacitor plates 5 emerges here at right angles from the first connection plate 11. A multiplicity of second capacitor plates 13 correspondingly also emerges at right angles from the second connection plate 12. The first and second capacitor plates 5, 13 are arranged parallel and spaced apart one on top of the other. In this arrangement of the capacitor plates, the first plates 5 engage in a comb-like fashion in the second plates 13. First capacitor plates 5 and second capacitor plates 13 are therefore arranged adjacent to one another in an alternating fashion.

The first capacitor plates 5 are connected to the same electrical potential via the first connection plate 11 and the first electrical terminal 6. The second capacitor plates 13 are, in contrast, connected via the second connection plate 12 and the second electrical terminal 7 to a common electrical potential, which is different from the electrical potential of the first capacitor plates 5. This ensures that in each case adjacent capacitor plates 5, 13 are connected to a different electrical potential and an electrical voltage is therefore respectively provided between these plates. Apart from the bottom and the top capacitor plate in FIG. 2, the plates therefore have a double-sided action. The capacitor therefore has a relatively large capacitance per volume. As a result, extraneous influences, for example, induced extraneous fields, have only a small effect on the measurement. It is therefore possible to dispense with costly screening measures.

During operation of the device, the engine oil is directed through the device in the direction of flow 3, the oil flowing through between the capacitor plates 5, 13. While the engine oil is located between the capacitor plates 5, 13, the capacitance of the capacitor which is formed by the plates 5, 13 is determined by the evaluation device 10. When the fuel portion in the engine oil changes, the dielectric constant of the engine oil and therefore the measured capacitance changes. The fuel portion in the engine oil is in turn determined from the measured capacitance by the evaluation device 10 based on characteristic diagrams which are preferably determined in the scope of a preceding calibration process.

To identify the type of the fuel present in the engine oil, alternating voltages at different frequencies are applied to the capacitor plates 5, 13 by the evaluation device 10.

In particular, in this context an alternating voltage frequency region is passed through. The impedance of the capacitor is likewise respectively determined for the different alternating voltage frequencies by the evaluation device 10. An impedance spectrum is therefore recorded. On the basis of the impedance spectrum, the type of fuel which is located in the engine oil is then identified by the evaluation device 10. For this purpose, the evaluation device 10 evaluates, inter alia, the position and level of maxima and minima of the impedance spectrum. In the illustrated example, the evaluation is carried out by a comparison with impedance spectrums for known levels of fuel contamination which have previously been produced in the scope of a calibration process.

The device according to the invention and the method according to the invention permit the fuel portion in the engine oil to be reliably determined in a simple and cost-effective way.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for determining a percentage of fuel in an engine oil of a motor vehicle, comprising:
   introducing the engine oil between at least two electrodes that form a capacitor;
   providing an initial calibration step to obtain calibration data;
   determining a capacitance of the capacitor while the engine oil is present between the at least two electrodes;
   determining the percentage of fuel in the engine oil based on the capacitance of the capacitor and the calibration data;
   applying alternating voltages of different frequencies to the at least two electrodes;
   determining an impedance of the capacitor for each respective frequency to generate an impedance spectrum; and
   identifying a specific type of fuel present in the engine oil based on minima and maxima of the impedance spectrum.

2. The method as claimed in claim 1, wherein the engine oil is introduced between a plurality of electrodes configured to form the capacitor.

3. The method as claimed in claim 1, wherein the electrodes are capacitor plates.

4. The method as claimed in claim 3, wherein the capacitor plates are arranged in parallel and spaced apart from one another.

5. A device for determining a percentage of fuel in an engine oil of a motor vehicle, comprising:
- at least two electrodes configured to form a capacitor and have the engine oil placed therebetween;
- a voltage supply configured to provide alternating voltages of different frequencies to the at least two electrodes; and
- an evaluation device coupled to the at least two electrodes configured to determine:
  - a capacitance of the capacitor while the engine oil is located between the electrodes,
  - initial calibration data at an initial calibration operation,
  - the percentage of fuel in the engine oil based on the capacitance of the capacitor and the initial calibration data,
  - an impedance of the capacitor for each of the alternating voltages of different frequencies and to generate an impedance spectrum, and
  - a specific type of the fuel present in the engine oil based at least in part on minima and maxima of the impedance spectrum.

6. The device as claimed in claim 5, wherein the electrodes are capacitor plates.

7. The device as claimed in claim 5, wherein a plurality of electrode plates form the capacitor.

8. The device as claimed in claim 7, wherein the capacitor plates are arranged in parallel and spaced apart from one another.

9. The method as claimed in claim 2, wherein the plural electrodes are capacitor plates.

10. A device for determining a percentage of fuel in an engine oil of a motor vehicle, comprising:
- a first terminal plate;
- a second terminal plate substantially parallel and spaced apart from the first electrode plate;
- a plurality of first electrodes arranged parallel to and spaced apart from one another extending from the first terminal plate towards the second terminal plate;
- a plurality of second electrodes extending from the second terminal plate towards the first terminal plate, the plural second electrodes arranged parallel to and spaced apart from the plural first electrodes;
- a voltage supply configured to provide alternating voltages of different frequencies to the first and the second terminal plates; and
- an evaluation device coupled to the first and the second terminal plates configured to determine:
  - a capacitance between the plural first and second electrodes while the engine oil is located between the plural first and second electrodes,
  - initial calibration data at an initial calibration operation,
  - the percentage of fuel in the engine oil based on the capacitance and the initial calibration data,
  - an impedance of the capacitor for each of the alternating voltages of different frequencies and generate an impedance spectrum, and
  - a specific type of the fuel present in the engine oil based at least in part on minima and maxima of the impedance spectrum.

11. The device as claimed in claim 10, further comprising a housing configured to guide the engine oil between the plural first and second electrodes.

12. The method as claimed in claim 2, further comprising determining at least one of an initial capacitance and initial impedance of the engine oil.

13. The device as claimed in claim 8, wherein the capacitor plates are one of flat and curved.

14. The device as claimed in claim 11, wherein the housing is one of cubic and cylindrical.

* * * * *